United States Patent
Anand

(10) Patent No.: US 10,890,639 B2
(45) Date of Patent: Jan. 12, 2021

(54) CORRELATION OF BRAIN IMAGING AND PERIPHERAL BLOOD GENE EXPRESSION COMPONENTS TO IDENTIFY MOLECULAR SIGNATURES OF CNS DRUG EFFECTS

(71) Applicant: THE CLEVELAND CLINIC FOUNDATION, Cleveland, OH (US)

(72) Inventor: Amit Anand, Pepper Pike, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 16/413,896

(22) Filed: May 16, 2019

(65) Prior Publication Data

US 2019/0353729 A1  Nov. 21, 2019

Related U.S. Application Data

(60) Provisional application No. 62/672,246, filed on May 16, 2018.

(51) Int. Cl.
*G01V 3/00* (2006.01)
*G01R 33/48* (2006.01)
(Continued)

(52) U.S. Cl.
CPC ........ *G01R 33/4806* (2013.01); *A61B 5/0042* (2013.01); *A61B 5/055* (2013.01);
(Continued)

(58) Field of Classification Search
CPC ............. G01R 33/543; G01R 33/5659; G01R 33/3415; G01R 33/36; A61B 5/055
(Continued)

(56) References Cited

U.S. PATENT DOCUMENTS

| | | | | |
|---|---|---|---|---|
| 2007/0105105 A1* | 5/2007 | Clelland | ............... | C12C 1/6809 |
| | | | | 435/6.14 |
| 2008/0241839 A1* | 10/2008 | Potkin | .................. | C12Q 1/6881 |
| | | | | 435/6.16 |

OTHER PUBLICATIONS

Altinay, Murat, et al. "Quetiapine extended release open-label treatment associated changes in amygdala activation connectivity in anxious depression: an fMRI study." Journal of Clinical Psychopharmacology 36.6 (2016): 562-571.
(Continued)

*Primary Examiner* — Walter L Lindsay, Jr.
*Assistant Examiner* — Frederick Wenderoth
(74) *Attorney, Agent, or Firm* — Tarolli, Sundheim, Covell & Tummino LLP

(57) ABSTRACT

Systems and methods are provided for correlating functional magnetic resonance imaging (fMRI) with gene expression. Brains of first and second sets of patients are imaged at first and second times to provide first and second sets of fMRI images. Blood is drawn from each of the first and second sets of patients at the first and second times to provide first and second sets of gene expression transcripts. A therapeutic is administered to the first set of patients between the first and second times. A change in the connectivity of the brain for each patient is determined from the first and second sets of fMRI images. A set of changes in the peripheral lymphocyte gene expression that are correlated with changes in the connectivity of the brain are determined from the change in the connectivity of the brain for each patient and the collected imaging and gene expression data.

1 Claim, 1 Drawing Sheet

(51) Int. Cl.
  *C12Q 1/6876* (2018.01)
  *A61B 5/055* (2006.01)
  *A61B 5/00* (2006.01)

(52) U.S. Cl.
  CPC ...... *C12Q 1/6876* (2013.01); *A61B 2576/026* (2013.01); *C12Q 2600/158* (2013.01)

(58) Field of Classification Search
  USPC .................................................... 324/309
  See application file for complete search history.

(56) References Cited

OTHER PUBLICATIONS

Amico, Enrico, et al. "Mapping the functional connectome traits of levels of consciousness." Neuroimage 148 (2017): 201-211.

Anand, Amit, et al. "Effects of lithium monotherapy for bipolar disorder on gene expression in peripheral lymphocytes." Molecular neuropsychiatry 2.3 (2016): 115-123.

Anand, Amit, et al. "Antidepressant effect on connectivity of the mood-regulating circuit: an FMRI study." Neuropsychopharmacology 30.7 (2005): 1334-1344.

Anand, Amit M.D., "Lithium Monotherapy Modulation of Brain Structural and Functional Connectome: A Novel Drug Discovery Biomarker", Center for Behavioral Health, Cleveland Clinic Foundation, 1 page.

Anand, Amit, "Lithium Modulation of Functional Connectome & Peripheral Transcription—A Novel Treatment Biomarker", pp. 1-4.

Anand, Amit, et al. "Activity and connectivity of brain mood regulating circuit in depression: a functional magnetic resonance study." Biological psychiatry 57.10 (2005): 1079-1088.

Spielberg, Jeffrey M., et al. "Resting state brain network disturbances related to hypomania and depression in medication-free bipolar disorder." Neuropsychopharmacology 41.13 (2016): 3016-3024.

Dichter, Gabriel S., et al. "Functional neuroimaging of treatment effects in psychiatry: methodological challenges and recommendations." International Journal of Neuroscience 122.9 (2012): 483-493.

Hariri, Ahmad R., et al. "Brain-derived neurotrophic factor val66met polymorphism affects human memory-related hippocampal activity and predicts memory performance." Journal of Neuroscience 23.17 (2003): 6690-6694.

Ho, Beng-Choon, et al. "Cognitive and MRI Brain Morphometric Correlates of Brain-Derived Neurotrophic Factor Val66Met Gene Polymorphism in Schizophrenia and Healthy Volunteers." Archives of general psychiatry 63.7 (2006): 731.

Ortiz-Teran, Laura, et al. "Brain circuit—gene expression relationships and neuroplasticity of multisensory cortices in blind children." Proceedings of the National Academy of Sciences 114.26 (2017): 6830-6835.

Pearlson, Godfrey D., Vince D. Calhoun, and Jingyu Liu. "An introductory review of parallel independent component analysis (p-ICA) and a guide to applying p-ICA to genetic data and imaging phenotypes to identify disease-associated biological pathways and systems in common complex disorders." Frontiers in genetics 6 (2015): 276.

* cited by examiner

CORRELATION OF BRAIN IMAGING AND PERIPHERAL BLOOD GENE EXPRESSION COMPONENTS TO IDENTIFY MOLECULAR SIGNATURES OF CNS DRUG EFFECTS

RELATED APPLICATIONS

This application claims priority to U.S. Provisional Patent Application Ser. No. 62/672,246 ("the '246 application"), filed May 16, 2018 and entitled CORRELATION OF BRAIN IMAGING AND PERIPHERAL BLOOD GENE EXPRESSION COMPONENTS TO IDENTIFY MOLECULAR SIGNATURES OF CNS DRUG EFFECTS. The entirety of the '246 application is hereby incorporated by reference.

TECHNICAL FIELD

This disclosure relates to medical imaging and, more particularly, to ultrasonic spectral parameter detection of different tissue types, machine learning for merging input data from multiple ultrasonic sources, and use of cepstral parameters to aid in differentiating between tissue types.

DETAILED DESCRIPTION

Figure 1:
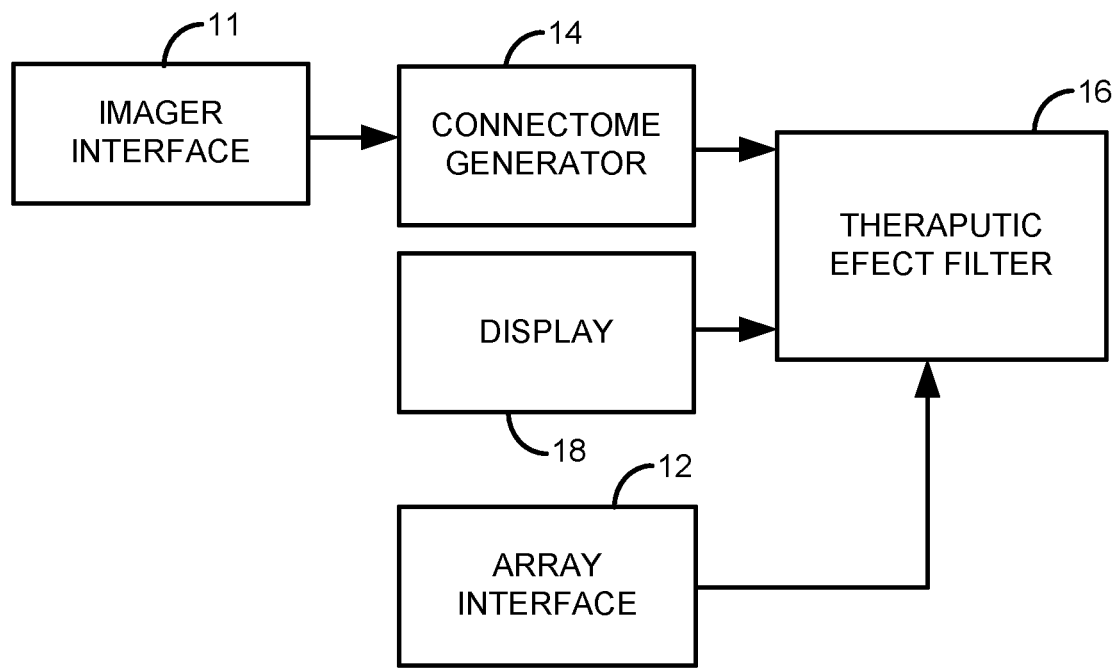
FIG. 1 illustrates a system for evaluating the effects of a therapeutic on a patient in accordance with an aspect of the present invention.

Systems and methods are provided for correlating changes in imaging with peripheral blood gene expression. Various forms of imaging, including functional and structural magnetic resonance imaging (MRI), can be used to determine functional, structural, and neurochemical changes in the brain, and a measure of the peripheral gene expression can be correlated with the imaging to determine a molecular signature of the effect of the drug on the brain. This molecular signature can then be verified in basic science studies and can be used to develop drugs. In one implementation, the imaging modality is functional magnetic resonance imaging (fMRI), with the image being evaluated via an independent component analysis (ICA) process. It is the resulting connectome that is correlated with the gene expression to determine the effects of the drug.

In one specific implementation, the effects of lithium on a patient can be evaluated. Lithium is effective for both the depressed and manic phases of bipolar disorder (BD). Furthermore, it is effective as a prophylactic treatment to prevent future manic and depressed episodes. Lithium is a life-saving medication as it has consistently been shown to decrease suicides as well as overall mortality in subjects who take it. However, despite decades of clinical use and research, the neural and molecular correlates of lithium effectiveness in bipolar disorder remain unclear. Most of the studies of effects of lithium on the brain and the underlying molecular effects have been done in animal models as brain biopsy in a living human brain is not possible due to ethical reasons.

The systems and methods presented herein were applied to investigate the effects of lithium on structural and functional brain imaging measures. Furthermore, a method to identify molecular pathways involved in lithium action was tested by correlating changes in brain imaging measures and peripheral gene expression to in vivo identify the molecular pathways involved in lithium action. This novel method can also be used in the future to identify molecular pathways involved in other developed and in development neuropharmacological agents. In this study, 23 medication free BP subjects as well as 13 closely matched healthy controls were included in a study. Patients were scanned at baseline and after 8 weeks of lithium treatment. Scans were performed using a Siemens 3T Tim Trio. A high resolution structural scan and a functional resting-scan was obtained using establisehd methods, for example, the methods described in Anand A, McClin5ck J, Murrell J, Karne H, Nurnberger J, Edenberg H. *Effects of Lithium Monotherapy for Bipolar Disorder on Gene Expression in Peripheral Lymphocytes. Molecular Neuropsychiatry.* 2016; 2(3): 115-123. (hereinafter "Anand 2016"). The entirety of the Anand 2016 publication is hereby incorporated by reference.

For structural data, voxel-based methodology (VBM) analysis was done using SPM8 software, and the resultant grey matter (GM) images from the segmented MPRAGE were normalized to MNI space and smoothed with 10 mm kernel. The difference between the images at two time points were created and then later used in the fusion analysis. For functional data, we investigated amygdala functional connecticivity. Prepocessing steps included, motion correction using SLice-Oriented MOtion COrrection (SLOMOCO) (Beall, 2010). Timeseries obtained from eroded white matter/ventricular masks were partialled (Jo et al, 2010), images normalized to MNI space using SPM (Penny et al, 2011), and bandpass filtered (0.008-0.08 Hz) via 3dBandpass (Cox, 1996). Participants with 5 motion-corrupted (>2 mm displacement) volumes were excluded from analysis (Jiang et al, 1995; Beall and Lowe, 2014). Left & right amygdalas were used as regions of interest (ROIs), the timeseries from these ROIs were extracted series from all subjects and whole brain voxel-wise correlation maps were generated using SPM separately for each ROI, which were then z-transformed and smoothed with 8 mm kernel. The difference between the images at two time points were created and then later used in the fusion analysis.

We investigated both individual transcript gene expression as well as gene expression pathways (See Anand 2016). The expression values for each subject from affymetrix gene chip was standardized across each gene. The average of the genes in the pathway were then calculated. The difference in the standardized values is then used as input in the gene modality of the fusion analysis. Lithium monotherapy was associated with changes within various resting state networks and in particular the task-positive network (p=0.05 corrected). Lithium monotherapy was associated with changes in the peripheral gene expression pathways (p=0.05). Changes in the functional connectome mediated the relationship between changes in gene expression and behavioral changes—mutlivariate regression analysis revealed significant correlation between fusion analysis imaging and gene components and changes in the Clinical Global Impression Scale (CGIS) for Bipolar Severity (p=0.05).

For data reduction a number of methods can be used. For this analysis for data reduction gene expression pathway data and imaging data we used Independent Component Analysis (ICA). To look at the relation between changes to treatment of BP with brain structural and functional connectivity with gene expression, we performed fusion analysis using Fusion ICA Toolbox (FIT). Parallel ICA option from FIT was used with GM images (week8—baseline) as one modality and (week8-baseline) of average standardized gene expression values of the 64 pathways described in Anand et al, 2016 as another modality. The same was done with left & right amygdalas separately.

FIG. 1 illustrates a system 10 for evaluating the effects of a therapeutic on a patient in accordance with an aspect of the present invention. It will be appreciated that the system 10 can be implemented as dedicated hardware, software instructions stored on a non-transitory medium and executed by an associated processor, or a combination of hardware and software. An imager interface 11 receives images of the brains of each of a first set of patients and a second set of patients using functional magnetic resonance imaging (fMRI) at a first time to provide a first set of fMRI images. Similarly, an assay interface 12 receives data representing a peripheral lymphocyte gene expression of each of the first set of patients and the second set of patients, measured, via blood withdrawn from the patient at the first time, to provide a first set of gene expression transcripts. A therapeutic can be administered to the first set of patients at a second time that is after the first time. After this, the imager interface 11 receives images of the brains of each of the first set of patients and the second set of patients using functional magnetic resonance imaging (fMRI) at a third time to provide a second set of fMRI images. Similarly, the assay interface 12 receives data representing a peripheral lymphocyte gene expression of each of the first set of patients and the second set of patients, measured, via blood withdrawn from the patient at the third time, to provide a second set of gene expression transcripts.

Each of the first set of fMRI images and the second set of fMRI images are provided to a connectome generator 14 that determines, from the first set of fMRI images and the second set of fMRI images, a change in the connectivity of the brain for each of the first set of patients and the second set of patients. A therapeutic effect filter 16 determines, from the change in the connectivity of the brain for each of the first set of patients and the second set of patients, the first set of gene expression transcripts, and the second set of gene expression transcripts, a set of changes in the peripheral lymphocyte gene expression that are correlated with changes in the connectivity of the brain.

In one implementation, resting state whole brain connectivity was measured using Independent Component Analysis implemented within Group ICA fMRI Toolbox (GIFT) (Calhoun et al http://mialab.mrn.org/software/fit/index.html) and differences between previously described networks investigated. Peripheral gene expression (RNA) analysis was conducted using Ingenuity Canonical Pathway Analysis software. RNA transcripts which showed a difference before and after treatment were included for pathway analysis and pathways showing significant differences (p=0.05) were included in the analysis. A composite score for each pathway was calculated from the mean of treatment related difference in each of the transcripts present in the pathway. The effect of lithium was studied for the BP group as a whole while controlling for the effect of state using Repeated measures ANOVA (RMANOVA). Fusion analysis using parallel Independent Component Analysis (ICA) was conducted using Fusion ICA Toolbox (FIT) within GIFT. Once the set of changes in the peripheral lymphocyte gene expression that are correlated with changes in the connectivity of the brain is determined, it is displayed to a user at an associated display.

Figure 2:
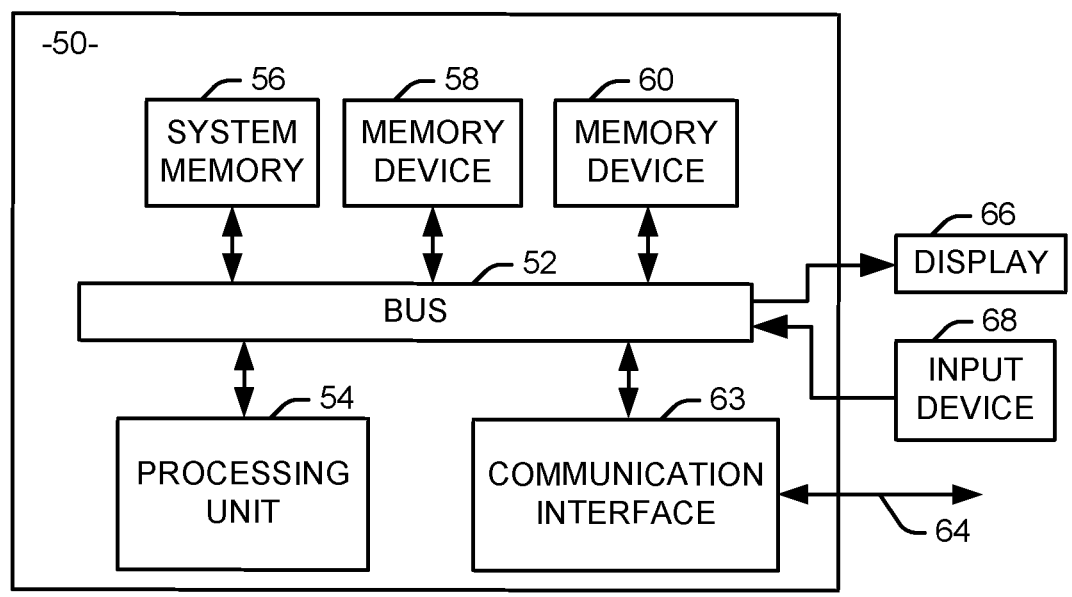
FIG. 2 is a schematic block diagram illustrating an exemplary system of hardware components capable of implementing examples of the system disclosed in FIG. 1.

FIG. 2 is a schematic block diagram illustrating an exemplary system 50 of hardware components capable of implementing examples of the system disclosed in FIG. 1. The system 50 can include various systems and subsystems. The system 50 can be a personal computer, a laptop computer, a workstation, a computer system, an appliance, an application-specific integrated circuit (ASIC), a server, a server blade center, a server farm, etc.

The system 50 can includes a system bus 52, a processing unit 54, a system memory 56, memory devices 58 and 60, a communication interface 62 (e.g., a network interface), a communication link 64, a display 66 (e.g., a video screen), and an input device 68 (e.g., a keyboard and/or a mouse). The system bus 52 can be in communication with the processing unit 54 and the system memory 56. The additional memory devices 58 and 60, such as a hard disk drive, server, stand-alone database, or other non-volatile memory, can also be in communication with the system bus 52. The system bus 52 interconnects the processing unit 54, the memory devices 56-60, the communication interface 62, the display 66, and the input device 68. In some examples, the system bus 52 also interconnects an additional port (not shown), such as a universal serial bus (USB) port.

The processing unit 54 can be a computing device and can include an application-specific integrated circuit (ASIC). The processing unit 54 executes a set of instructions to implement the operations of examples disclosed herein. The processing unit can include a processing core.

The additional memory devices 56, 58 and 60 can store data, programs, instructions, database queries in text or compiled form, and any other information that can be needed to operate a computer. The memories 56, 58 and 60 can be implemented as computer-readable media (integrated or removable) such as a memory card, disk drive, compact disk (CD), or server accessible over a network. In certain examples, the memories 56, 58 and 60 can comprise text, images, video, and/or audio, portions of which can be available in formats comprehensible to human beings. Additionally or alternatively, the system 50 can access an external data source or query source through the communication interface 62, which can communicate with the system bus 52 and the communication link 64.

In operation, the system 50 can be used to implement one or more parts of a therapeutic evaluation system in accordance with the present invention. Computer executable logic for implementing the various functions described in FIG. 1 resides on one or more of the system memory 56, and the memory devices 58, 60 in accordance with certain examples. The processing unit 54 executes one or more computer executable instructions originating from the system memory 56 and the memory devices 58 and 60. The term "computer readable medium" as used herein refers to any medium that participates in providing instructions to the processing unit 54 for execution, and it will be appreciated that a computer readable medium can include multiple computer readable media each operatively connected to the processing unit.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method comprising:

imaging the brains of each of a first set of patients and a second set of patients using functional magnetic resonance imaging (fMRI) at a first time to provide a first set of fMRI images;

measuring, via blood withdrawn from the patient, a peripheral lymphocyte gene expression of each of the first set of patients and the second set of patients at the first time to provide a first set of gene expression transcripts;

administering a therapeutic to the first set of patients at a second time that is after the first time;

imaging the brains of each of the first set of patients and the second set of patients using fMRI at a third time that is after the second time to provide a second set of fMRI images;

measuring, via blood withdrawn from the patient, the peripheral lymphocyte gene expression of each of the first set of patients and the second set of patients at the third time to provide a second set of gene expression transcripts;

determining, from the first set of fMRI images and the second set of fMRI images, a change in the connectivity of the brain for each of the first set of patients and the second set of patients; and determining, from the change in the connectivity of the brain for each of the first set of patients and the second set of patients, the first set of gene expression transcripts, and the second set of gene expression transcripts, a set of changes in the peripheral lymphocyte gene expression that are correlated with changes in the connectivity of the brain.

* * * * *